United States Patent [19]

Spona et al.

[11] Patent Number: 5,583,129
[45] Date of Patent: Dec. 10, 1996

[54] COMPOSITION FOR CONTRACEPTION

[76] Inventors: Jürgen Spona, Billrothstrasse 78, A-1190 Vienna, Austria; Bernd Düsterberg, Spirdingseestrasse 27, D-12307 Berlin, Germany; Frank Lüdicke, c/o Hopital Cantonal Universitaire, 32bis, Bld de la Cluse, CH-1211 Geneva 4, Switzerland

[21] Appl. No.: 268,996

[22] Filed: Jun. 30, 1994

[30] Foreign Application Priority Data

Dec. 22, 1993 [DE] Germany ............... 43 44 462.8

[51] Int. Cl.⁶ .................. A61K 31/56; A61K 31/57; A61K 31/585
[52] U.S. Cl. ............... 514/178; 514/173; 514/182
[58] Field of Search ............... 514/178, 182, 514/173

[56] References Cited

FOREIGN PATENT DOCUMENTS

| 0253607 | 1/1988 | European Pat. Off. . |
| 0491415 | 6/1992 | European Pat. Off. . |
| 0491438 | 6/1992 | European Pat. Off. . |

OTHER PUBLICATIONS

Parke Davis package insert for Loestrin, Jun., 1993.

G. B. Melis, et al., Contraception, "*A Comparative Study on the Effects fo a Monophasic Pill Containing Desogestrel Plus 20 μg Ethinylestradiol, a Triphasic Combination Containing Levonorgestrel and a Monophasic Combination Containign gestrodene on Coagulatory Factors*", vol. 43, No. 1, pp. 23–30 (Jan. 1991).

A. R. Genazzani, et al. (Ed), Progress in Gynecology and Obstetrics, "*Multicenter Clinical Trial on the new Oral Contraceptive 20 μg Ethinylestradiol*", Chapter 1, pp. 747–756, (1990).

*Primary Examiner*—Phyllis G. Spivack
*Attorney, Agent, or Firm*—Millen, White, Zelano, & Branigan, P.C.

[57] ABSTRACT

This invention relates to a method of inducing contraception comprising administering an estrogen selected from 2.0 to 6.0 mg of 17β-estradiol and
0.015 to 0.020 mg of ethinylestradiol;

and a gestagen selected from 0.05 to 0.075 mg of gestodene,
0.075 to 0.125 mg of levonorgestrel,
0.06 to 0.15 mg of desogestrel,
0.06 to 0.15 mg of 3-ketodesogestrel,
0.1 to 0.3 mg of drospirenone,
0.1 to 0.2 mg of cyproterone acetate,
0.2 to 0.3 mg of norgestimate and
>0.35 to 0.75 mg of norethisterone for a female of reproductive age, who has not yet reached premenopause, by administration for 23 or 24 days, beginning on day one of the menstrual cycle, followed by 5 or 4 pill-free or sugar pill days, during a total of 28 days in the administration cycle.

8 Claims, 1 Drawing Sheet

COMPOSITION FOR CONTRACEPTION

DESCRIPTION

This invention relates to the common use of estrogens and gestagens for the production of a combination preparation for oral contraception and a corresponding pack containing this combination preparation.

Combination preparations for oral contraception are already known, for example, Femovan® [DE-PS 2 546 062] or Marvelon® [DE-OS 2 361 120]. These preparations consist of 21 active ingredient-containing (estrogen/gestagen) dosage units and 7 active ingredient-free coated tablets (sugar pills; placebos). The dose to be administered daily is uniformly high in each case (so-called single-phase preparations) and produces the desired contraceptive effect in the entire intake period and in the intake pause or during the intake of the placebos. In most preparations, a 7-day interruption of the intake of active ingredient-containing dosage units was considered necessary until quite recently to trigger a reliable withdrawal bleeding and thus to achieve a satisfactory cycle control.

Other preparations, which exhibit more than 21 dosage units containing an estrogenic and progestational active ingredient, and in which the intake pause is partially (Ijzerman, Pasquale) or completely (Kuhl) bridged over by estrogen-containing dosage units. In this case, it is possible that the synthetic estrogen ethinylestradiol otherwise contained in oral contraceptives is replaced partially or completely by a conjugated estrogen, preferably estradiol.

A combination preparation for substitution therapy and contraception for females before menopause (approximately starting from the 40th year of life) is known from EP-A-0 253 607. This combination preparation contains an estrogen from the group 17β-Estradiol, ethinylestradiol and mestranol as well as a gestagen from the group levonorgestrel, gestodene, desogestrel, 3-ketodesogestrel and norethindrone.

A thus selected composition is to offset hormonal irregularities in the transition phase of premenopause and to help alleviate the symptoms caused by the hormonal changeover of the female organism in this phase. Such a composition simultaneously assures a premenopausal female the contraceptive protection still necessary at this age.

The development of new oral contraceptives for females of reproductive age before premenopause was characterized during the last twenty years above all by the reduction of the estrogen and gestagen dosages.

The reduction of the daily hormone dose was connected with the expectation to minimize the frequency of undesired side effects. Epidemiological data collected in the meantime confirm the desired trend toward better compatibility of lower-dosed preparations relative to cardiovascular complications [(1.) Thorogood, M., Oral Contraceptives and Cardiovascular Disease: An Epidemiologic Overview; Pharmacoepidemiology and Drug Safety, Vol. 2: 3–16 (1993); (2.) Gerstman, B. B.; Piper, J. M.; Tomita, D. K.; Ferguson, W. J.; Stadel, B. V.; Lundin, F. E.; Oral Contraceptive Estrogen Dose and the Risk of Deep Venous Thromboembolic Disease, Am. J. E., Vol. 133, No. 1, 32–36 (1991); (3.) Lidegaard, O., Oral contraception and risk of a cerebral thromboembolic attack: results of a case-control study; BMJ Vol. 306, 956–63 (1993); (4.) Vessey, M.; Mant, D.; Smith, A.; Yeates, D.; Oral contraceptives and venous thromboembolism: findings in a large prospective study; BMJ, Vol. 292, (1986); (5.) Mishell, D. R., Oral Contraception: Past, Present and Future Perspectives; Int. J. Fertil., 36 Suppl., 7–18 (1991)].

It is assumed that a correlation exists above all between the level of the estrogen dose and the incidence of cardiovascular diseases. But the maintenance of the contraceptive effectiveness stands in the way of an extreme reduction of the daily estrogen dose. Although the ovulation-inhibiting effect of the low-dosed oral contraceptives is caused mainly by the gestagenic component, the estrogenic component also makes a significant contribution to the central inhibition action and to the ovarian suppression (ovulation inhibition). Moreover, the daily estrogen dose must not fall below the minimum dose ranges, so that a satisfactory cycle control can be assured (Der Frauenarzt [The Gynecologist]; 34, 7: 793 (1993)].

The lowest estrogen dose contained in an oral contraceptive on the market at this time is 20 μg of ethinylestradiol, combined with 150 μg of desogestrel (Mercilon). Although the cycle control of this preparation is, as expected, somewhat poorer in comparison to preparations with a higher estrogen dose, the high acceptance rate of Mercilon indicates a small clinical relevance of this drawback. But the observation, made identically in several studies, of a lesser ovarial suppression of the preparation containing 20 μg of ethinylestradiol represents a clinically important problem. Obviously with this very low estrogen dose, in the case of many females, the maturation of follicles, which could be detected with ultrasonic studies or hormonal studies, results [(6.) Lunell, N. O.; Carlström, K.; Zador, G.; Ovulation inhibition with a combined oral contraceptive containing 20 μg of ethinylestradiol and 250 μg of levonorgestrel; Acta. Obstet. Gynecol. Scand. Suppl. 88: 17–21 (1979); (7.) Mall-Haefeli, M.; Werner-Zodrow, I.; Huber, P. R.; Klinische Erfahrungen mit Mercilon und Marvelon unter besonderer Berücksichtigung der Ovar-Funktion [Clinical Experience with Mercilon and Marvelon under special consideration of the ovary function]; Geburtsh. und Frauenheilk. [Obstetrics and Gynecology] 51, 35–38, Georg Thieme Verlag, Stuttgart-New York (1991); (8.) Strobel, E., Behandlung mit oralen Kontrazeptiva [Treatment with Oral Contraceptives]; Fortschr. Med. Vol. 110, No. 20 (1992); (9.) Letter to Editor, Contraception 45: 519–521 (1992); (10.) Teichmann, A. T.; Brill, K.; Can Dose Reduction of Ethinylestradiol in OCs Jeopardize Ovarian Suppression and Cycle Control? Abstract Book, VIIIth World Congress on Human Reproduction, Bali, Indonesia (1993)].

The hormone determinations performed showed that functional granulosa cells that secrete 17β-estradiol are involved. Each intake error in the case of females with clear ovarian activity, thus with follicular maturations, can result in a quick increase of gonadotropin production. The requirements for an ovulation would thus be present. It is estimated that approximately one third of females take oral contraceptives irregularly within one year of use (Gynpress, Volume 1, No. 3, 1990). The risk of a pregnancy is therefore high especially in the case of intake errors with the 20 μg ethinylestradiol preparations.

The object of this invention is an improved single-phase combination preparation for a female of reproductive age, who is not yet in premenopause, containing an estrogen and gestagen in each individual dosage unit, with the lowest possible estrogen content in each individual dosage unit, but also with a low total hormone content per administration cycle.

It has now been found that a pronounced ovarian suppression without frequent follicular maturations with low daily estrogen dosage, low total estrogen as well as low total hormone amount per administration cycle can be achieved by the use of a composition comprising an estrogen selected from 2.0 to 6.0 mg of 17β-estradiol and 0.015 to 0.020 mg of ethinylestradiol;

and a gestagen selected from 0.05 to 0.075 mg of gestodene, 0.075 to 0.125 mg of levonorgestrel, 0.06 to 0.15 mg of desogestrel, 0.06 to 0.15 mg of 3-ketodesogestrel, 0.1 to 0.3 mg of drospirenone, 0.1 to 0.2 mg of cyproterone acetate, 0.2 to 0.3 mg of norgestimate and >0.35 to 0.75 mg of norethisterone.

for the production of a form of dosage for contraception for a female of reproductive age, who has not yet reached premenopause, by administration of the form of dosage for 23 or 24 days, beginning on day one of the menstrual cycle (first day of menstrual bleeding), followed by 5 or 4 pill-free or sugar pill days, during a total of 28 days in the administration cycle.

The terms "premenopause" and "menopause" are used within the scope of this invention in the meaning of the conventional definition, see, for example, "The Controversial Climacteric," P.A. of Keep et al., Ed., MTP press (1981), e.g., p. 9.

The daily hormone dose is kept to a very low level here, while the usual 21-day intake is extended by two or three days. The remaining 5 or 4 days of a cycle are preferably bridged over by placebos, to avoid intake errors, or by 5 or 4 intake-free days.

According to a preferred embodiment of this invention, this relates to the use of a composition comprising an estrogen selected from >2.0 to 6.0 mg of 17β-estradiol and 0.020 mg of ethinylestradiol;

and a gestagen selected from

>0.06 to 0.075 mg of gestodene,

>0.100 to 0.125 mg of levonorgestrel,

>0.10 to 0.15 mg of desogestrel,

>0.10 to 0.15 mg of 3-ketodesogestrel, 0.25 to 0.30 mg of drospirenone, 0.1 to 0.2 mg of cyproterone acetate, 0.2 to 0.3 mg of norgestimate and 0.50 to 0.75 mg of norethisterone for the production of a form of dosage for contraception as described above.

In addition, this invention relates to a combination product for oral contraception, which comprises a) 23 or 24 dosage units, each containing an estrogen selected from >2.0 to 6.0 mg of 17β-estradiol and 0.020 mg of ethinylestradiol;

and a gestagen selected from

>0.06 to 0.075 mg of gestodene,

>0.100 to 0.125 mg of levonorgestrel,

>0.10 to 0.15 mg of desogestrel,

>0.10 to 0.15 mg of 3-ketodesogestrel, 0.25 to 0.30 mg of drospirenone, 0.1 to 0.2 mg of cyproterone acetate, 0.2 to 0.3 mg of norgestimate and 0.50 to 0.75 mg of norethisterone and b) 5 or 4 sugar pills or other indications to show that the daily administration of 23 or 24 dosage units is to be followed by 5 or 4 pill-free or sugar pill days are to be followed.

Further embodiments according to the invention follow from the features of the subclaims.

An especially preferred combination preparation according to this invention comprises 23 dosage units, each containing 20 μg of ethinylestradiol and 75 μg of gestodene and 5 sugar pills or other indications to show that no dosage unit or a sugar pill is administered during the last 5 days of the menstrual cycle.

The clinical study briefly described below was performed with ethinylestradiol as estrogen and gestodene as representative of the substance class of the gestagens possible according to the invention. All possible combinations of ethinylestradiol or estradiol according to the invention in the indicated dosages with one of the selected gestagens in the indicated dosages as 23- or 24-day preparations exhibit the advantages according to the invention.

The 23-day administration of 20 μg of ethinylestradiol in combination with 75 μg of gestodene results, in comparison to the 21-day administration, in a stronger ovarian suppression. In a double-placebo, randomized study on healthy females with normal ovarian function, groups of 30 test subjects each received the combination preparation either once daily over 21 or 23 days as well as placebos on 7 or 5 days (to assure the double-placebo nature of the study).

The treatment began after an ovulatory, untreated preliminary cycle on the first day of the menstrual bleeding of the subsequent cycle and extended altogether over three treatment cycles. The study was concluded with an untreated follow-up cycle.

The ovarian suppression was measured based on the level of the endogenous 17β-estradiol level and the size of follicular structures. The results show that the 17μ-estradiol levels with 23-day intake of the test preparation were significantly lower (p<0.05) in comparison to the 21-day administration (FIG. 1).

In accordance with this finding, the number of females with follicular maturations was also clearly higher in the 21-time administration relative to the 23-time administration (FIG. 2).

The intake interval extended only by two days surprisingly produces a significantly greater ovarian suppression with unchangingly low daily doses. The combination preparation according to the invention thus achieves the effectiveness previously known for preparations with a daily content of 30 μg of ethinylestradiol, although the daily ethinylestradiol dose is 33% lower and also the total dose per cycle is 27% lower.

The advantages of a combination preparation for oral contraception to be administered over 23 days relative to the usual 21-day preparations with less than 30 μg of ethinylestradiol can be characterized as follows:

1. A significantly lower frequency of follicular developments in the user (maximum of 13% in females who received the 23-day preparation relative to a maximum of 40% among those who received the 21-day preparation). This means a greater contraceptive reliability of the 23-day preparation, especially in the case of previous intake errors. The danger of "breakthrough ovulations" is smaller.

2. The occurrence of large follicles of more than a 30 mm diameter is extremely rare. The development of ovarian cysts is improbable with the 23-day preparation in comparison to the 21-day preparation.

3. The recruitment of dominant follicles is suppressed in the shortened intake-free pause.

4. The endogenous 17β-estradiol levels are suppressed easily controllably in the case of the majority of the users of the 23-day preparation. Clinical symptoms such as breast tenseness, premenstrual syndrome and menstrual disorders, which can be attributed to increased and greatly fluctuating estrogen levels, are observed with the 23-day preparation with clearly lower frequency.

In summary, an intake, extended by two (or three) days, of preparations containing 20 μg of ethinylestradiol in each daily dosage unit can produce the above-mentioned advantages, without the daily dose having to be raised to the previously largely used level of 30 μg of ethinylestradiol.

The formulation of an estrogen and gestagen for the use according to the invention or for a combination preparation according to the invention takes place completely analogously as it is already known for usual oral contraceptives with 21-day intake period of the active ingredients, such as, for example, Femovan® (ethinylestradiol/gestodene) or Microgynon® (ethinylestradiol/levonorgestrel).

A pack containing a combination preparation according to the invention is also designed analogously to packs for already known oral contraceptives on the market with the variation that instead of the usual 21 dosage units containing the active components, now 23 or 24 such dosage units and 5 or 4 sugar pills are present or else contain other suitable indications that 5 or 4 days are to be bridged over until continuation of the intake of active ingredient-containing dosage units.

Moreover, reference is made to the statements made in EP-A 0 253 607, especially also to the statements there for determination of equivalent amounts of ethinylestradiol and 17β-estradiol, on the one hand, and various gestagens, such as levonorgestrel, desogestrel, 3-ketodesogestrel and gestodene, on the other hand.

For further details for the determination of dose equivalents of various gestagenic active ingredients, reference is made to "Probleme der Dosisfindung: Sexualhormone" [Problems of Dose-Finding: Sex Hormones]; F. Neumann et al. in "Arzneimittelforschung" (Pharmaceutical Agent Research) 27, 2a, 296–318 (1977), as well as to "Aktuelle Entwicklungen in der hormonalen Kontrazeption" [Current Developments in Hormonal Contraception]; H. Kuhl in Gyn äkologe" [Gynecologist] 25: 231–240 (1992).

Figure 1:
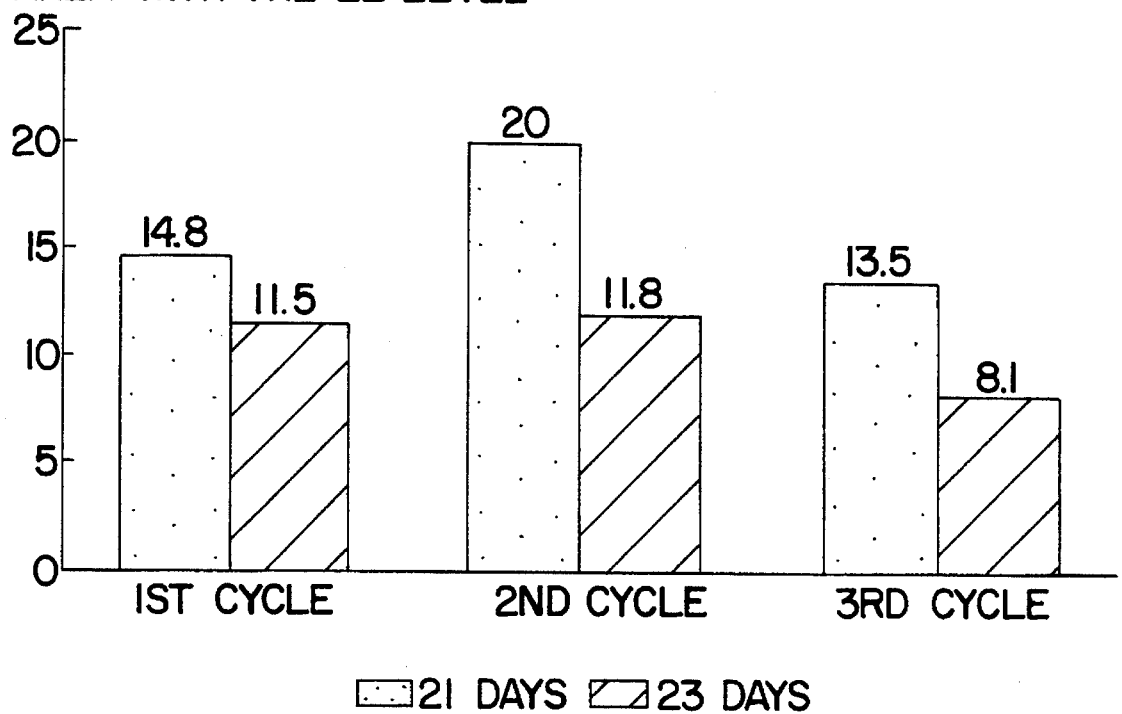
FIG. 1: Area with the 17β-estradiol level in groups of 30 females, who are treated with an oral contraceptive (75 μg of gestodene +20 μg of ethinylestradiol) in 21- or 23-day administration interval over three cycles.
Figure 2:
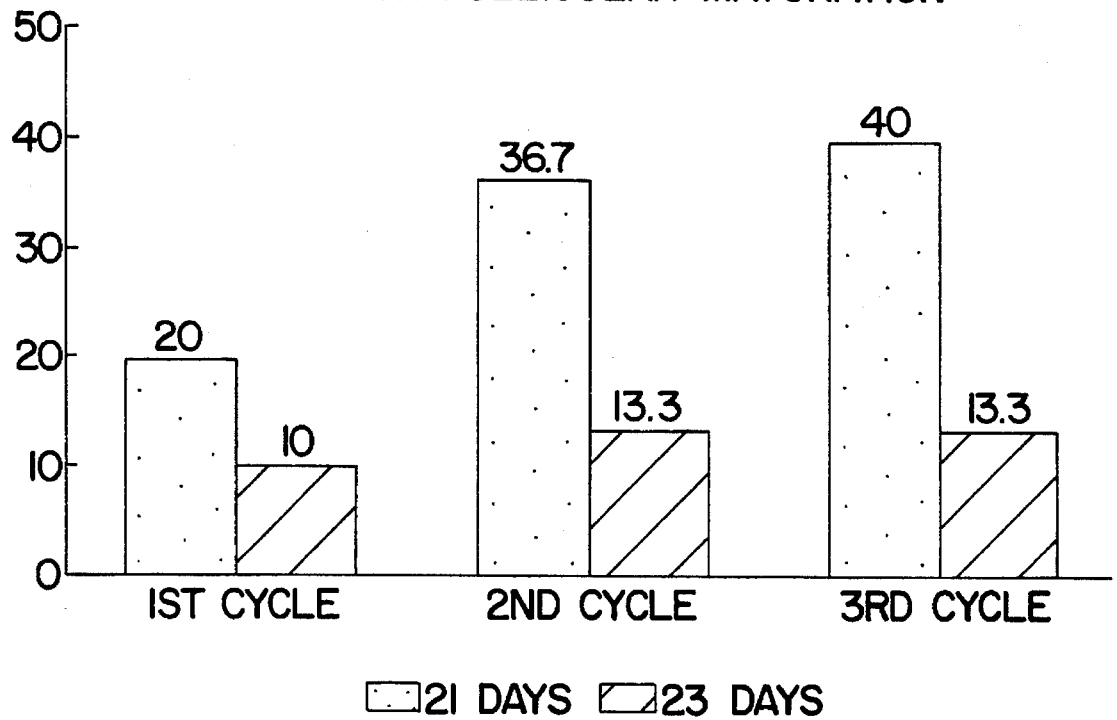
FIG. 2: Number of females in %, who showed follicular developments (>13 mm diameter) with 21- or 23-day treatment with an oral contraceptive (75 μg of gestodene +20 μg of ethinylestradiol).

We claim:

1. A method of inducing contraception in a female of reproductive age who has not yet reached premenopause, comprising administering to said female a composition comprising an estrogen selected from 2.0 to 6.0 mg of 17β-estradiol and 0.015 to 0.020 mg of ethinylestradiol;

and a gestagen selected from 0.05 to 0.075 mg of gestodene, 0.075 to 0.125 mg of levonorgestrel, 0.06 to 0.15 mg of desogestrel, 0.06 to 0.15 mg of 3-ketodesogestrel, 0.1 to 0.3 mg of drospirenone, 0.1 to 0.2 mg of cyproterone acetate, 0.2 to 0.3 mg of norgestimate and >0.35 to 0.75 mg of norethisterone;

wherein the composition is administered for 23 or 24 days, beginning on day one of the menstrual cycle, followed by 5 or 4 pill-free or sugar pill days, during a total of 28 days in the administration cycle.

2. A method according to claim 1, whereby the estrogen is ethinylestradiol.

3. A method according to claim 1, whereby the estrogen is 17β-estradiol.

4. A method according to claim 1, whereby the gestagen is gestodene.

5. A method according to claim 1, whereby the gestagen is levonorgestrel.

6. A method according to claim 1, whereby the gestagen is cyproterone acetate or drospirenone.

7. A method according to claim 1, whereby the composition comprises an estrogen selected from >2.0 to 6.0 mg of 17β-estradiol and 0.020 mg of ethinylestradiol;

and a gestagen selected from

>0.06 to 0.075 mg of gestodene,

>0.100 to 0.125 mg of levonorgestrel,

>0.10 to 0.15 mg of desogestrel,

>0.10 to 0.15 mg of 3-ketodesogestrel, 0.25 to 0.30 mg of drospirenone, 0.1 to 0.2 mg of cyproterone acetate, 0.2 to 0.3 mg of norgestimate and 0.50 to 0.75 mg of norethisterone.

8. A method according to claim 1, whereby the estrogen is present in a dose of 20 μg of ethinylestradiol or an equivalent dose of 17β-estradiol and the gestagen is present in a dose of 75 μg of gestodene or an equivalent dose of levonorgestrel, cyproterone acetate or drospirenone.

* * * * *